US010223782B2

(12) United States Patent
Sungkorn et al.

(10) Patent No.: US 10,223,782 B2
(45) Date of Patent: Mar. 5, 2019

(54) DIGITAL ROCK PHYSICS-BASED TREND DETERMINATION AND USAGE FOR UPSCALING

(71) Applicant: Ingrain, Inc., Houston, TX (US)

(72) Inventors: Radompon Sungkorn, Houston, TX (US); Jonas Toelke, Houston, TX (US); Yaoming Mu, Houston, TX (US); Carl Sisk, Indianapolis, IN (US); Abraham Grader, Houston, TX (US); Sneha Bhakta, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 29 days.

(21) Appl. No.: 15/300,759

(22) PCT Filed: Mar. 30, 2015

(86) PCT No.: PCT/US2015/023420
§ 371 (c)(1),
(2) Date: Sep. 29, 2016

(87) PCT Pub. No.: WO2015/153506
PCT Pub. Date: Oct. 8, 2015

(65) Prior Publication Data
US 2017/0018073 A1 Jan. 19, 2017

Related U.S. Application Data

(60) Provisional application No. 61/972,983, filed on Mar. 31, 2014.

(51) Int. Cl.
G06T 7/00 (2017.01)
G01N 33/24 (2006.01)
(Continued)

(52) U.S. Cl.
CPC ......... *G06T 7/0004* (2013.01); *G01N 15/088* (2013.01); *G01N 33/24* (2013.01);
(Continued)

(58) Field of Classification Search
CPC . G06T 2207/20021; G06T 2207/20016; G06T 2207/10056; G06T 2207/130181;
(Continued)

(56) References Cited

U.S. PATENT DOCUMENTS 6,516,080 B1 2/2003 Nur
2011/0246161 A1* 10/2011 Morton ................. E21B 49/00
703/9

(Continued)

FOREIGN PATENT DOCUMENTS

EA 200701136 A1 7/2012
WO 2015/153506 10/2015

OTHER PUBLICATIONS

"AU Patent Examination Report", dated Apr. 7, 2017, Appl No. 2015241030, "Digital Rock Physics-based Trend Determination and Usage for Upscaling," Filed Mar. 30, 2015, 3 pgs.
(Continued)

Primary Examiner — Ping Y Hsieh
(74) Attorney, Agent, or Firm — Chamberlain Hrdlicka

(57) ABSTRACT

An example method includes acquiring two-dimensional (2D) or three-dimensional (3D) digital images of a rock sample. The method also includes selecting a subsample within the digital images. The method also includes deriving a trend or petrophysical property for the subsample. The method also includes applying the trend or petrophysical property to a larger-scale portion of the digital images.

20 Claims, 10 Drawing Sheets

(51) Int. Cl.
  *G01N 15/08* (2006.01)
  *G06K 9/52* (2006.01)
  *G06K 9/62* (2006.01)
  *G06T 7/20* (2017.01)
(52) U.S. Cl.
  CPC ............ *G06K 9/52* (2013.01); *G06K 9/6267* (2013.01); *G06T 7/20* (2013.01); *G06T 2207/10056* (2013.01); *G06T 2207/20016* (2013.01); *G06T 2207/20021* (2013.01); *G06T 2207/30181* (2013.01)
(58) Field of Classification Search
  CPC ......... G06T 7/004; G06T 7/20; G06T 7/0004; G01N 15/088; G01N 33/24; G06K 9/52; G06K 9/6267
  See application file for complete search history.

(56) References Cited

U.S. PATENT DOCUMENTS

| | | | |
|---|---|---|---|
| 2012/0221306 A1* | 8/2012 | Hurley | G01V 99/005 703/6 |
| 2013/0179080 A1 | 7/2013 | Skalinski et al. | |
| 2017/0108483 A1* | 4/2017 | Clark | G01N 33/24 |

OTHER PUBLICATIONS

"PCT International Search Report and Written Opinion", dated Jun. 25, 2015, Appl No. PCT/US2015/023420, "Digital Rock Physics-based Trend Determination and Usage for Upscaling," filed Mar. 30, 2015, 11 pgs.

* cited by examiner

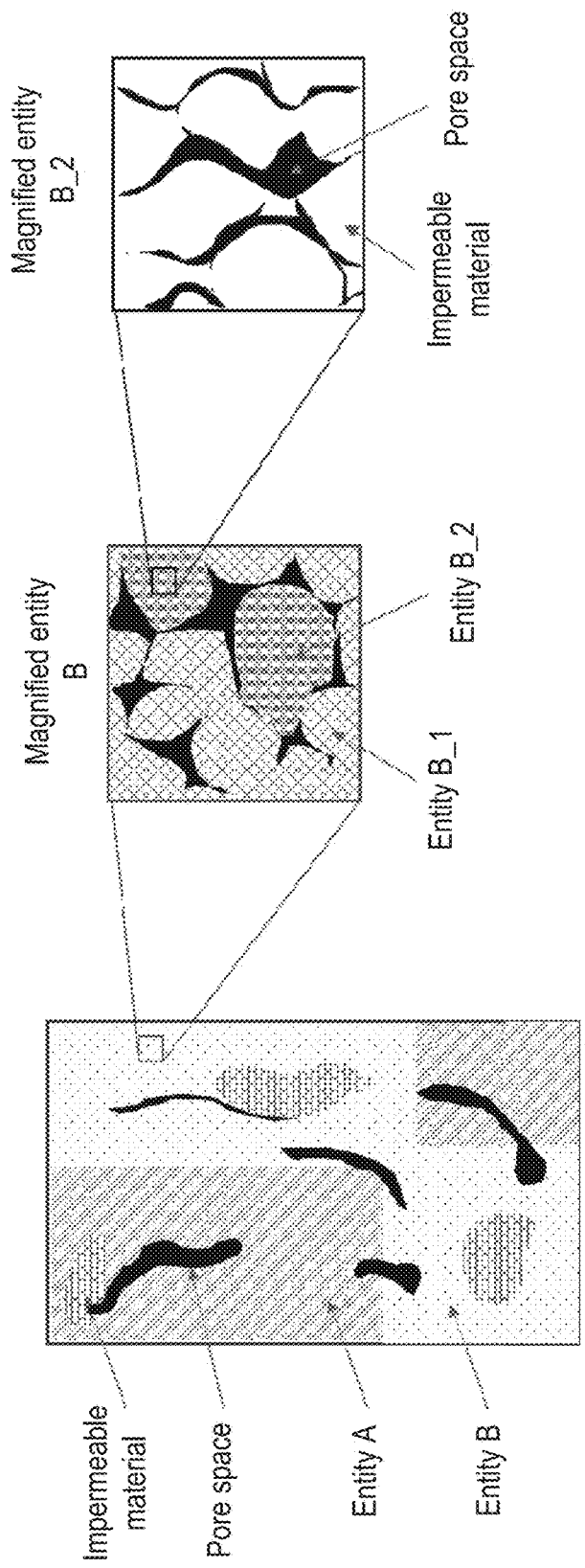

Course grid of image acquired for a large-scale sample

Fine grid of high-resolution image acquired for an entity

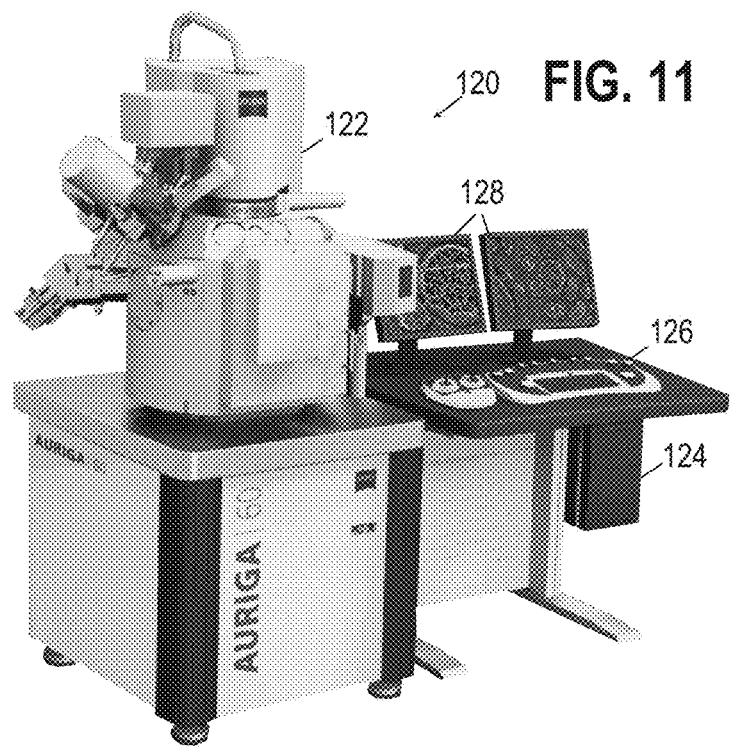
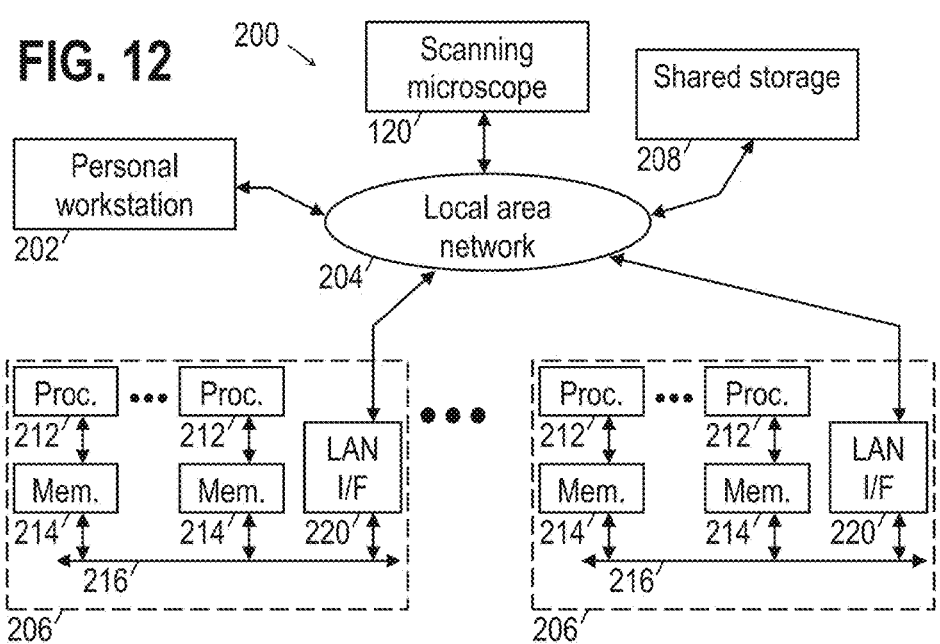

DIGITAL ROCK PHYSICS-BASED TREND DETERMINATION AND USAGE FOR UPSCALING

CROSS-REFERENCE TO RELATED APPLICATIONS

The present application claims priority to U.S. Pat. App. 61/972,983 titled "Digital Rock Physics-Based Trend Determination and Usage for Upscaling", filed Mar. 31, 2014 by inventors Radompon Sungkorn, Jonas Toelke, Yaoming Mu, Carl Sisk, and Avrami Grader, which is incorporated by reference in its entirety.

BACKGROUND

The relationships (also termed "trends") between petrophysical properties such as porosity, permeability, formation factor, elastic properties, relative permeability, and capillary pressure, are useful for various geological and engineering applications (Nelson, 1994), and are regarded as crucial to the to accurate characterization and evaluation of rocks/reservoirs, by which a thorough understanding is achieved. However, many factors such as degree of heterogeneity, rock formation, pore geometry, grain size, packing and solution/dissolution, cause the trends to vary in a complex manner (Ma and Morrow, 1996).

Scientists and engineers have employed various experimental approaches to establish trends (see, e.g. Ma & Morrow, 1996, Ehrenberg & Nadeau, 2005, Weibel et al., 2012, Vik et al., 2013, Torabi et al., 2013). The data resulting from these approaches generally has a large amount of scatter and deviation that make it difficult to discern any well-defined trends (Weibel et al., 2012). Additionally, such experiments often require weeks and large number of samples to establish a statistically meaningful trend, and consequently are vulnerable to experimental errors and difficulties.

Such issues can be avoided with the use of digital rock physics (DRP), which employs advanced imaging technologies, such as microscopy and spectroscopy, to construct a digital representation of the rock or other material at a chosen level of magnification and resolution. The digital representation includes, but is not limited to, a two- or three-dimensional image of a sample of the material. Computerized analysis techniques may then be applied to the acquired image to visualize the internal structure and/or to characterize the material. Depending on the analysis, a number of characteristic properties are measured, quantified, and inter-related. Even in the absence of experimental error, however, existing analysis techniques fail to suitably account for heterogeneities and other complicating factors that make it difficult to discern meaningful trends.

Moreover, while some useful characterization and conclusions may be derived from analysis of samples that can be directly magnified and imaged, the scale of a reservoir and its component formations is much too large to be directly imaged and analyzed. Nor is it feasible to perform a sufficient number of experiments on a large enough scale to extract trend information. Yet the importance of such large scale trend information to accurate reservoir evaluation and forecasting cannot be overemphasized. The main complicating factor for the determination of such trend information is the high degree of structural heterogeneity that is present in most reservoir rocks (Worthington, 2004), i.e. such rocks include more than one typical pore size and structure.

Numerous upscaling techniques for predicting large scale petrophysical properties from sample-derived trend information have been presented in the literature. A majority of these techniques are restricted to the study of the single-phase permeability of a porous material. For example, Durlofsky (Durlofsky, 2005) compared a variety of approaches for gridding and upscaling geocellular models for flow simulation. Khalili et al. (Khalili et al., 2012) established porosity transforms between high-resolution (small scale) and low-resolution (large scale) images to calibrate a low resolution porosity map, which can then be used to populate permeability on the low-resolution image. Renormalization schemes for upscaling have been proposed by Green & Paterson (Green & Paterson, 2007) and Krabbenhoft & Karim (Krabbenhoft & Karim, 2010). The conclusion of each of the studies above are similar: the results are sensitive to property contrasts, i.e., the range between the lowest and highest values, which depends strongly on the degree of heterogeneity of the porous material. More importantly, they found that the translation between large-scale and small-scale sample permeability varies greatly from sample to sample. In at least some cases, the large-scale sample tends to have a higher permeability that would be predicted by the small scale sample (Ehrenberg, 2007). Clearly, the existing methods fail to sufficiently resolve the relevant petrophysical properties in a manner suitable for upscaling.

SUMMARY

Accordingly, there is presented herein a statistical analysis method that, when applied to a digital representation of a rock, extracts a maximum amount of trend information, including the identification of heterogeneous regions of the sample and trend information associated therewith. Consequently multiple trends may be obtained from a given sample. Such additional trend information also enables a novel upscaling method that better transforms small scale trend information to larger scales by accounting for the heterogeneity found at each scale. The upscaling method is expressible in a recursive form to enable upscaling to occur at multiple scales so that, for example, reservoir-scale information might be derived from sample information obtained at sub-millimeter scales. With such information, reservoirs can be more accurately evaluated and produced.

BRIEF DRAWING DESCRIPTION

FIG. 7 shows sample images taken at multiple scales.

Figure 9:
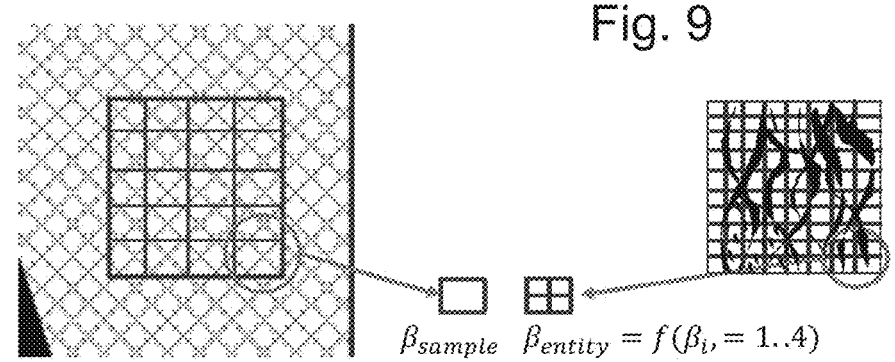
Figure 10:
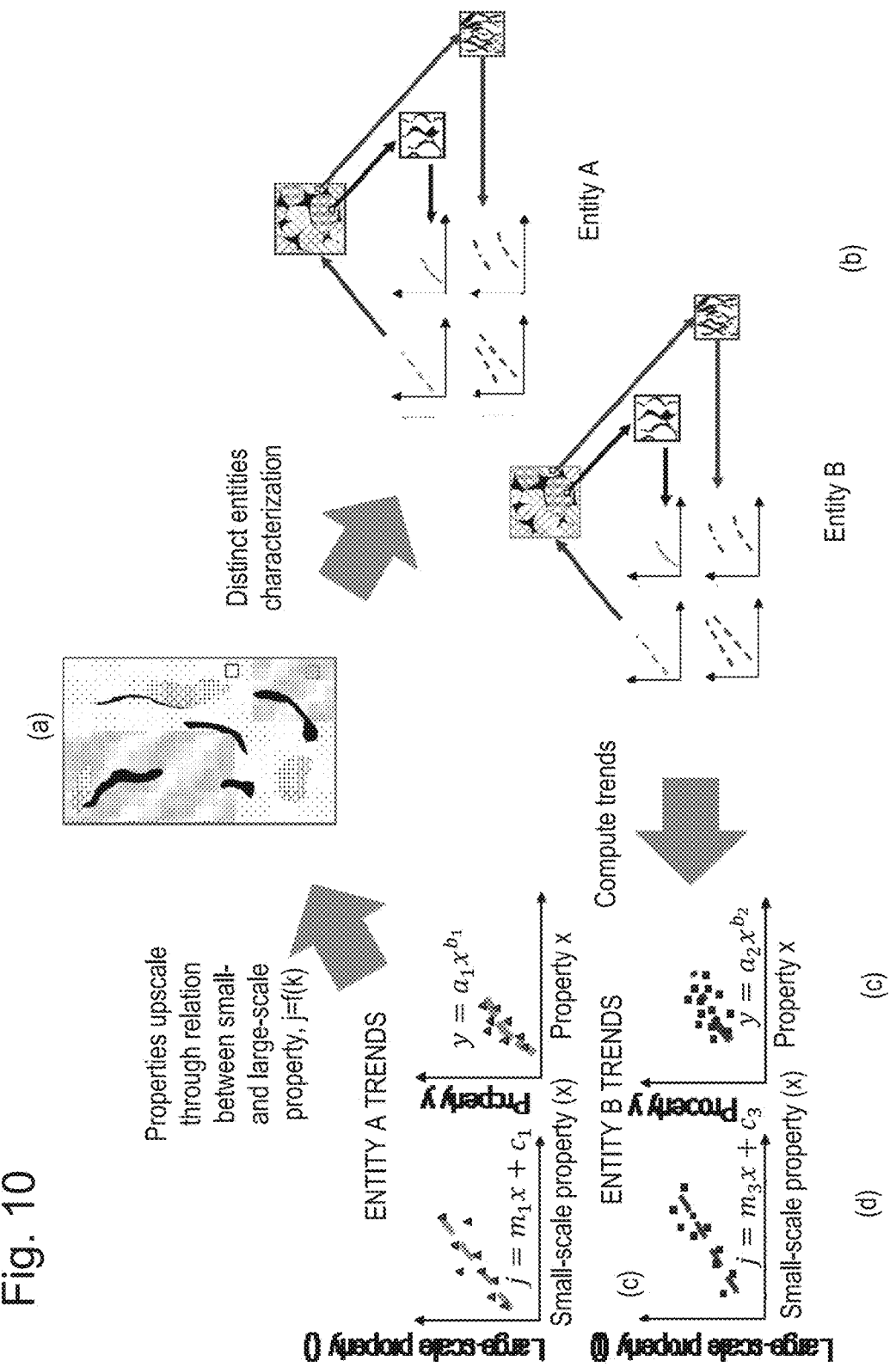

FIG. 9 relates images of two different scales.

FIGS. 10A-10D shows a second illustrative upscaling procedure.

FIG. 11 is an illustrative imaging system.

FIG. 12 is an illustrative computer system for implementing the disclosed methods.

DETAILED DESCRIPTION

Figure 1A:
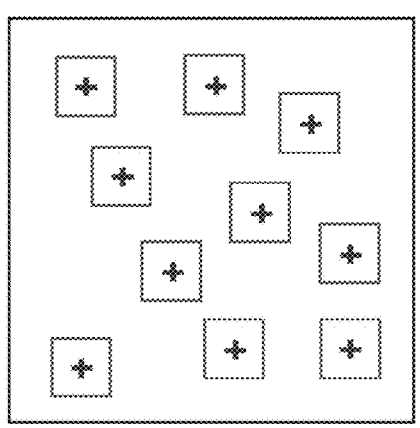
FIGS. 1A-1B show an illustrative relationship of two- and three-dimensional samples to multiple subsamples.
Figure 1B:
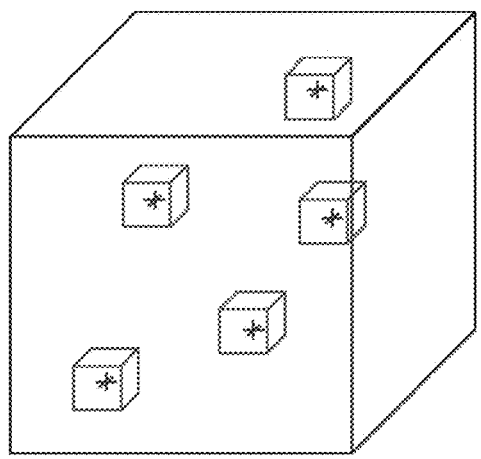

FIG. 1A shows a two-dimensional digital representation of a material, while FIG. 1B shows a three-dimensional digital representation. These representations are hereafter referred to as images. While it is possible to use raw images, the disclosed methods are facilitated by classifying each pixel as one of multiple phases, e.g., pore space, solid. Some embodiments may include additional phases indicating intermediate levels of porosity between open pore space and fully filled solid space, e.g., low density porous matrix, high density porous matrix. Within each image, a number of subsample positions are selected. The selection may be made randomly or systematically, and in an overlapping or non-overlapping fashion. Typically, the subsample regions are square (for two-dimensional images) or cubes (for three-dimensional images).

Figure 2:
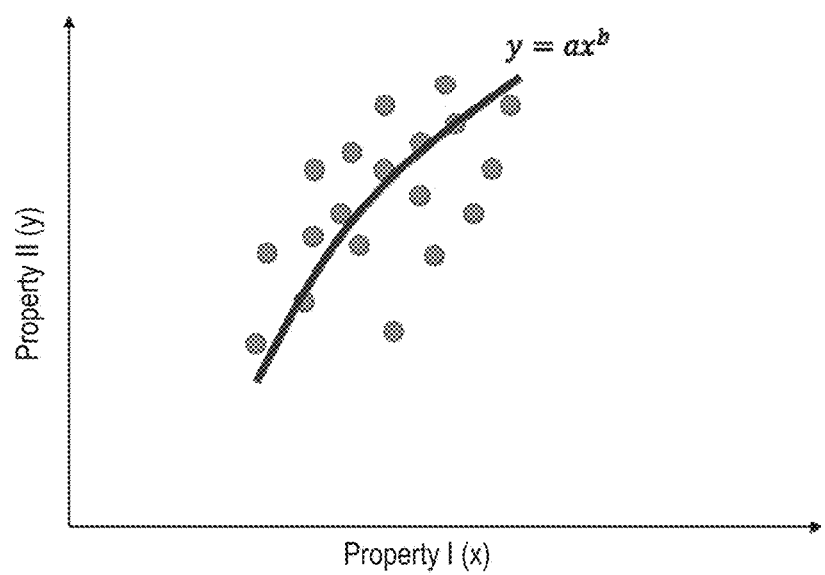
FIG. 2 shows an illustrative (single-component) trend.

The method then determines the properties of interest for each subsample. Properties commonly subjected to trend analysis in the petroleum industry are porosity vs. permeability, porosity vs. formation factor, and permeability vs. formation factor. The property measurements for all subsamples are then collected and analyzed to discern trend information. FIG. 2 shows a crossplot of two properties that suggests the presence of a trend, and further shows a parameterized curve that might be fit to the points representing the properties for each subsample. In at least some embodiments, the extracted trend information is presented in a mathematical form expressing the relationship between two properties.

Figure 3A:
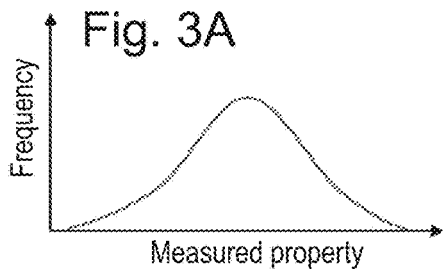
FIGS. 3A-3D show illustrative uni- and multi-mode distributions of one and more variables.
Figure 3B:
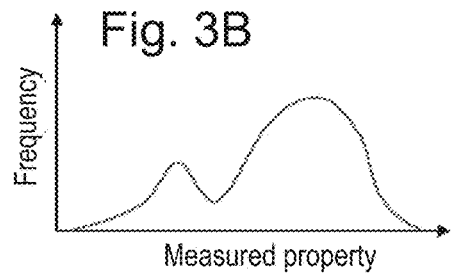
Figure 3D:
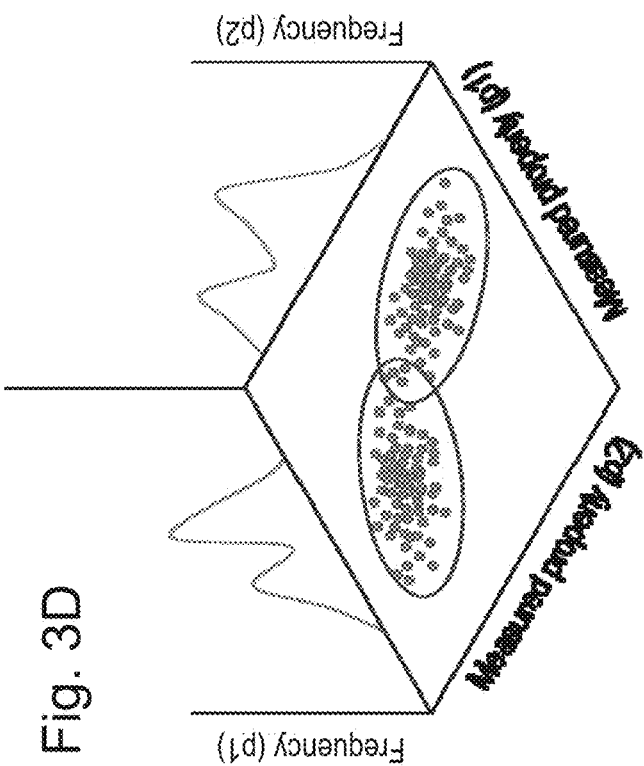
Figure 3C:
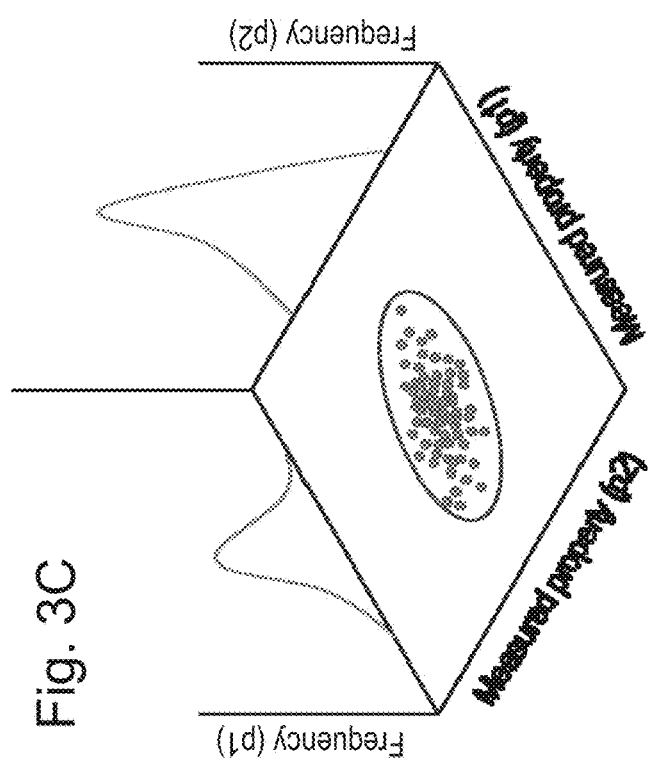

Due to its computerized implementation, the digital rock physics (DRP) approach offers a way to generate trends in fast, safe, and repeatable fashion. Most importantly, owing to the use of subsampling, trends can be generated with far fewer samples than most experimental methods, possibly as few as one sample. However, existing DRP methods assume that the sample is relatively homogeneous sample, i.e. the properties can be represented using unimodal distribution such as that shown in FIG. 3A or 3C. Consequently, these method yield only one trend for each sample (Ramstad et al., 2010, Khalili et al., 2012, Khalili et al., 2013, De Prisco et al., 2013) and inevitably fail to properly characterize relatively heterogeneous samples.

As most formation rocks/reservoirs possess a high degree of heterogeneity, this circumstance creates difficulties. Bimodal distributions, such as those shown in FIG. 3B or 3D, trimodal distributions, or even higher, are typical. It would be desirable to have a trend analysis method that properly accounts for the heterogeneity and complexity of most samples. The proposed method accomplishes this by treating the property measurement distribution as a mixture of component distributions and subjecting the overall distribution to a statistical analysis that extracts the component distributions.

Figure 4A:
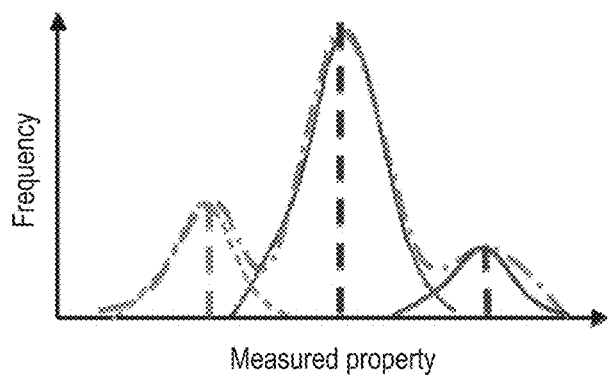
FIG. 4A shows a multi-mode distribution that is a mixture of multiple single-mode distributions.
Figure 4B:
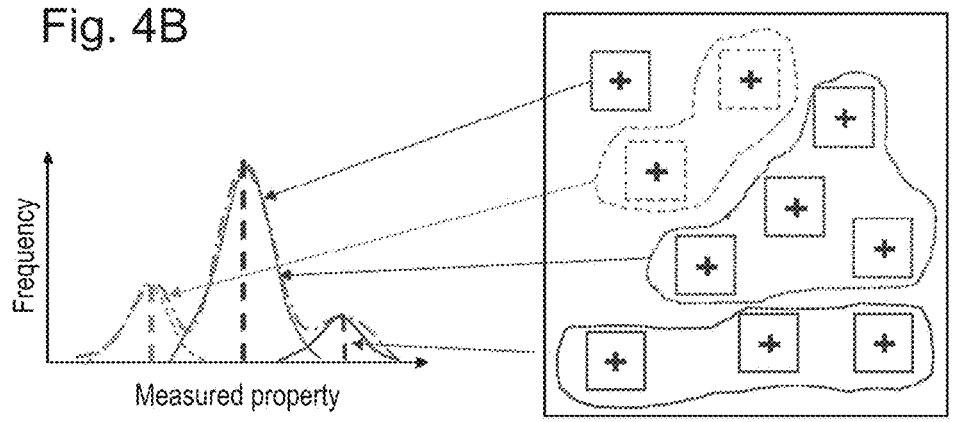
FIG. 4B shows the mapping of distribution components to spatial entities.

For example, FIG. 4A shows a trimodal distribution that is expressible as a weighted sum of three unimodal distributions. The statistical analysis determines the number of components, the position of each component, the size (variance) of each component, and the fraction (weight) of each component. (Suitable statistical analysis methods are discussed further below.) Once each component is identified, the points associated with that distribution may be determined, enabling the individual distributions to be mapped to the corresponding subsample positions as indicated in FIG. 4B. Note that the subsamples associated with a given component need not be contiguous.

Figure 5:
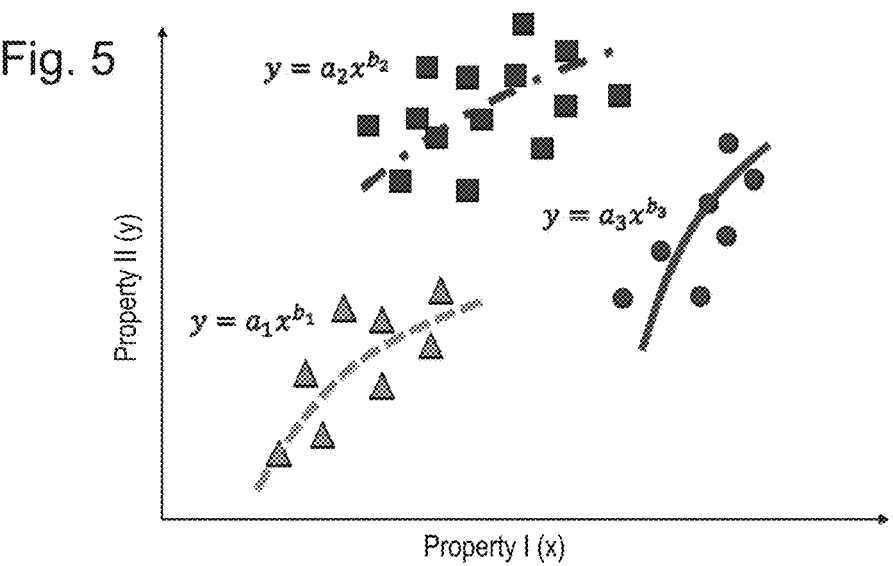
FIG. 5 shows an illustrative multi-component trend.

Having identified the components and their associated subsamples, a separate trend analysis may be performed for each component, as indicated in FIG. 5. A parameterized curve may be fit to the measurement points of each given component. Note that the fit of a single curve to the full set of measurement points would have obscured the sample's heterogeneity.

Figure 6A:
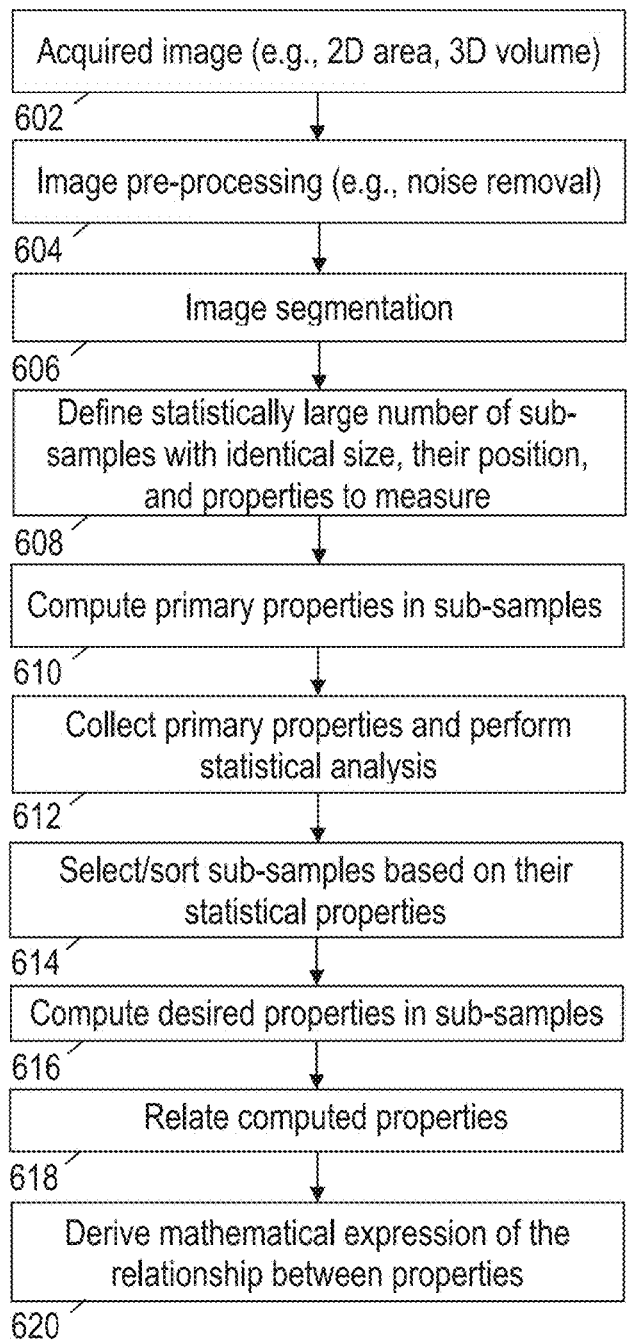
FIGS. 6A-6B are flow diagrams of illustrative trend determination methods.

FIG. 6A is a flow diagram of an illustrative trend determination method. In block 602, the method obtains a two dimensional or three dimensional image of a sample. In block 604, the image is pre-processed to remove noise and other artifacts of the imaging process. In block 606, the image is segmented, meaning that each pixel of the image is classified in to one of multiple possible categories, including at least pore (open space) and solid (filled spaced), and depending on resolution at the chosen magnification, possibly further including matrix phases of intermediate porosities between the two extremes.

In block 608, the method determines a statistically large number of subsamples, selecting their locations in a random or systematic and overlapping or non-overlapping fashion. Given the anticipated heterogeneity of the sample, it is desirable to have the density of subsample locations spread relatively evenly throughout the sample. The statistical largeness can be determined using well known statistical principles such as confidence levels and confidence intervals, or if feasible, the method may simply position the subsample locations to achieve complete (and possibly overlapping) coverage of the sample. The size of the subsamples may be selected arbitrarily or systematically (see, e.g. De Prisco et al., 2013) depending on the desired scale of information.

In block 610, the method computes the selected primary properties for each subsample. Examples of primary properties include porosity, pore structure, composition of porous matrices, and the computation may provide measurement of one or more such properties. In block 612, the distributions of the computed primary properties are determined and analyzed. Such distributions are typically multi-modal due to the typical sample's level of complexity and heterogeneity, and if multiple properties are measured, the distribution is multivariate. (FIGS. 3A-3D are examples of unimodal and multimodal as well as univariate and multivariate distributions.)

Suitable statistical analyses are those that can be applied to uni- or multi-modal and/or uni- or multi-variate distributions to determine the number of component distributions and the parameters associated with each. The analysis of a multimodal distribution should not result in only one mean value and standard deviation value, but rather it should yield a set of means, standard deviations, and relative weighting for each of multiple component distributions presented in the sample. The number of distributions indicates the number of distinct regions characterized by the chosen primary properties. Accordingly, regions with different characteristics can be identified within the sample by associating each individual subsample with a corresponding distribution and thereby mapping the distributions to specific locations in the image (block 614). It is possible for distinct regions to share a common distribution. For more information regarding property distribution analysis options, reference may be had to Radompon Sungkorn et al., "Representative Elementary Volume Determination Via Clustering-Based Statistics", PCT Application Serial Number PCT/US15/23419 and filed Mar. 30, 2015, and hereby incorporated herein by reference in its entirety.

In block 616, the method processes the subsamples associated with each component distribution in turn, to determine the desired secondary properties of those subsamples. Examples of secondary properties include permeability, formation factor, capillary pressure and relative permeability. Various numerical techniques such as finite volume method (FVM), finite element method (FEM) and lattice Boltzmann method (LBM) can be used for the computation of these properties.

For each given component distribution, the method associates the secondary property measurements with the primary property measurements (block 618) and applies a regression analysis to determine the relationships (block 620) between the primary and secondary properties. For example, one commonly used trend analysis employs a linear least square regression technique with a power function ($y=ax^b+c$) to derive the relationship between porosity and permeability. FIG. 5 shows an example of a system with three distinct structures/patterns (i.e. tri-modal distribution having three component distributions). The relationships between property I and property II are analyzed separately for each structures, yielding three trends for the sample.

Figure 6B:
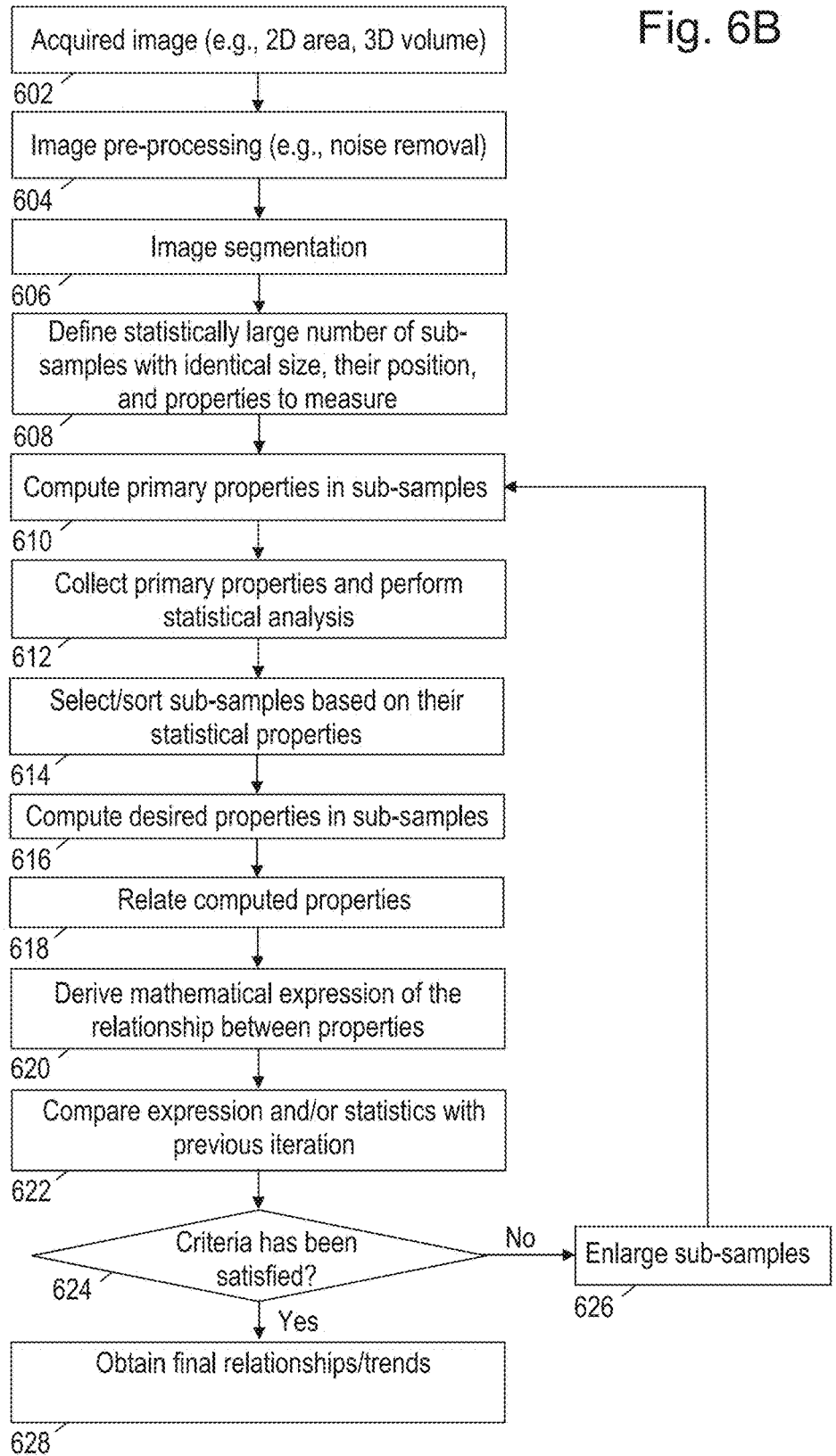

The trends identified by the method of FIG. 6A are expected to vary based on the subsample size. If it is desired to obtain trends that are relatively insensitive to subsample size, the method may be augmented as shown in FIG. 6B to find trends associated with the representative elementary volume (REV). Blocks 602-620 are the same as in FIG. 6A. Blocks 622-628 are added to provide a loop in which the trends are found for multiple subsample sizes. In block 622, the parameters of the mathematical expression (e.g., a, b, c, of the regression function $y=ax^b+c$) for each trend are compared to those of the previous loop iteration. If no previous iteration was performed, or if the parameters or the number of trends do not match the previous iteration, a decision is made in block 624 to repeat the loop. The method enlarges the subsample size in block 626 and blocks 610-624 are repeated with the new subsample size. Once a match is detected (indicating that the trends have converged to stability), the method outputs the trend information and the minimum corresponding subsample size in block 628. As an alternative to comparing expression parameters for the convergence test, the method may compare parameters of the component distributions identified by the analysis in block 612, and reserve the operations of blocks 614-620 for performance only after a suitable subsample size has been identified.

The foregoing trend determination methods enable a new framework for upscaling petrophysical properties, i.e., deriving large-scale properties from small scale samples analyzed with digital rock physics (DRP) imaging. FIG. 7 shows sample images acquired at three different scales: large scale (low resolution), intermediate scale (intermediate resolution), and small scale (high resolution). The use of small scale samples to derive the petrophysical properties of the large scale sample yields an enormous gain in computational efficiency.

Each sample image reveals the presence of multiple, distinguishable entities which can be identified using the foregoing methods, image processing-based techniques (e.g. Liang, 2012, Unser & Eden, 1989), or statistical analysis (see e.g. Christopher, 2003, Barker, 1998). Each entity can be classified as resolved or unresolved, the former indicating that the entity is substantially void (empty space) or substantially impermeable solid (filled space), and the latter indicating that the entity is a collection of porous matrices (partially filled space). As the relevant properties of the resolved entities are already apparent, subsequent analysis focuses on the unresolved entities.

The unresolved entities are selected arbitrarily or identified based on visual inspection or statistical analysis (potentially using the methods explained above). One or more higher-resolution samples are taken from each entity. In the example of FIG. 7, this yields the intermediate scale image which is not fully resolved. The process is repeated until, as shown by the small scale image on the right side of FIG. 7, a fully resolved sample is obtained. Two magnifications were employed in FIG. 7, and hence the upscaling process set out below will be repeated twice to obtain the desired petrophysical properties for the large scale image.

Figure 8:
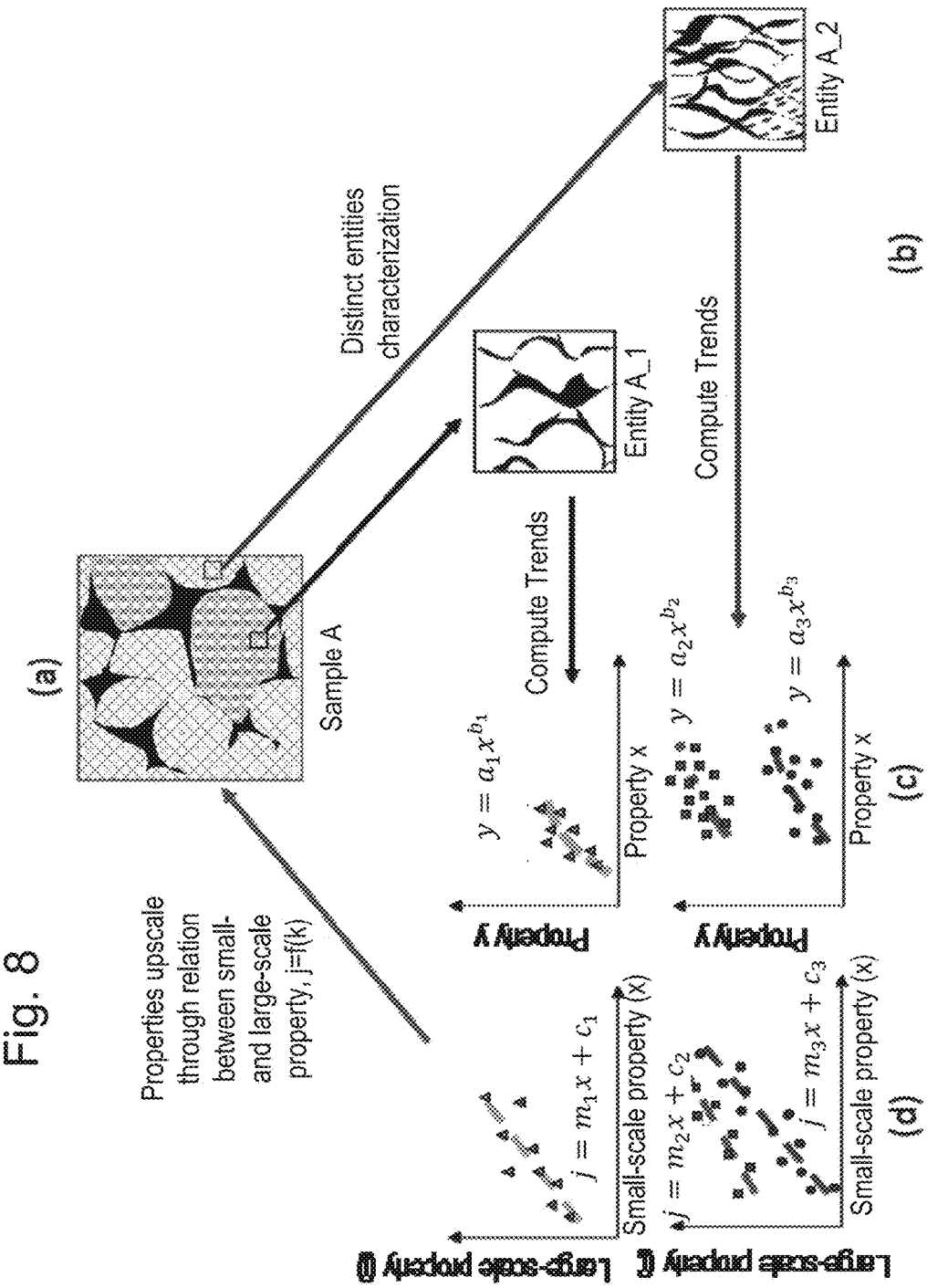
FIGS. 8A-8D show an illustrative upscaling procedure.

FIGS. 8A-8D shown the three phases associated with the first upscaling process. The first phase, represented by the arrow from FIG. 8A to FIG. 8B, is the obtaining of high resolution images from each of the unresolved entities. In the second phase, as represented by the arrows from FIG. 8B to FIG. 8C, the high resolution images are processed to measure their properties and to derive their inter-relationships using the trend-identification methods set out previously.

As set out previously, subsamples of the image are taken and sorted based on their structures/patterns and their location. Various numerical techniques such as finite volume method (FVM), finite element method (FEM) and lattice Boltzmann method (LBM) can be used to solve the governing equations of these properties. It is desirable to solve multi-scale governing equations, such as Darcy equations, Brinkman equations or Brinkman-Forchheimer equations for permeability. The relationships between properties are derived using a regression analysis techniques with a selected mathematical function, see FIG. 8C.

This populating operation may employ an image registration technique, i.e. a method to transform multiple images into similar frame of reference, but this is not necessary if the exact location of entities in the large sample are known. As indicated at FIG. 8D, the method then relates a property value of the larger scale image to the properties measured at the smaller scale, optionally in terms of a linear translation. For example, the pixel intensity of the larger scale image may be related to the porosity measured in a corresponding part of the smaller scale image. Such linear translations may be employed to map the properties revealed by the small scale trends of FIG. 8C to corresponding locations in the image of FIG. 8A, thereby providing petrophysical property measurements for each of the previously-identified (unresolved) entities of FIG. 8A.

As part of the trend-mapping, the third phase performs an aggregation operation. As shown in FIG. 9, each pixel of the larger scale image corresponds to multiple pixels of the smaller scale image. As the trend properties associated with the different small scale pixels may not be identical (e.g., at the boundary between entities), the aggregation operation combines the different trend properties to provide a suitable aggregated property measurement value. Direct area/volume averaging may be used or a wavelet decomposition technique may be employed. The trend information, together with the aggregation and translation processes, provide a transitive relationship for mapping petrophysical properties onto the larger scale image. This third phase may hereafter be referred to as "populating" the larger scale sample.

Once the upscaling process has been performed for each of the entities identified in each of the intermediate scale samples, the upscaling operation is performed again, using the populated intermediate scale samples as inputs as represented in FIGS. 10A-10D. The resulting populated large-scale sample can be used to resolve large-scale petrophysical properties and/or trends. If desired the method can be extended to ever-larger scales.

The foregoing methods may be computer implemented. For context, FIGS. 11-12 demonstrate an illustrative context for the use of these methods. FIG. 11 shows an illustrative high-resolution focused ion beam and scanning electron microscope 120 having an observation chamber 122 in which a sample of material is placed. A computer 124 is coupled to the observation chamber instrumentation to control the measurement process. Software on the computer 124 interacts with a user via a user interface having one or more input devices 126 (such as a keyboard, mouse, joystick, light pen, touchpad, or touchscreen) and one or more output devices 128 (such as a display or printer).

For high resolution imaging, the observation chamber 122 is typically evacuated of air and other gases. A beam of electrons or ions can be rastered across the sample's surface to obtain a high resolution image. Moreover, the ion beam energy can be increased to mill away thin layers of the sample, thereby enabling sample images to be taken at multiple depths. When stacked, these images offer a three-dimensional image of the sample to be acquired. As an illustrative example of the possibilities, some systems enable such imaging of a 40×40×40 micrometer cube at a 10 nanometer resolution.

However, the system described above is only one example of the technologies available for imaging a sample. Transmission electron microscopes (TEM) and three-dimensional tomographic x-ray transmission microscopes are two other technologies that can be employed to obtain a digital model of the sample. Regardless of how the images are acquired, the foregoing disclosure applies so long as the resolution is sufficient to reveal the porosity structure of the sample.

The source of the sample, such as in the instance of a rock formation sample, is not particularly limited. For rock formation samples, for example, the sample can be sidewall cores, whole cores, drill cuttings, outcrop quarrying samples, or other sample sources which can provide suitable samples for analysis using methods according to the present disclosure.

FIG. 12 is an example of a larger system 200 within which the scanning microscope 120 can be employed. In the larger system 200, a personal workstation 202 is coupled to the scanning microscope 120 by a local area network (LAN) 204. The LAN 204 further enables intercommunication between the scanning microscope 120, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the scanning microscope. For tasks having small computational demands, the software may be executed on the personal workstation 202, whereas computationally demanding tasks may be preferentially run on the high performance computing platform 206.

When adapted for use in the illustrative systems, the methods may be modified to enable one or more of the operations to be carried out concurrently to exploit the availability of parallel processing resources. Moreover, the order of the steps may vary, with some of the steps carried out in a potentially speculative fashion. Such variations are within the scope of the claims.

Potential advantages of the disclosed systems and methods include the use of DRP to overcome the obstacles presented by traditional experimental approaches and instead provide an accurate, safe, repeatable determination of petrophysical properties the accounts for the typical complexity and heterogeneity/anisotropy of the rocks/reservoirs. It provides a universal framework to establish trends between petrophysical properties, e.g. porosity, permeability, formation factor, elasticity, relative permeability.

The following references are hereby incorporated herein by reference in their entirety:

Barker, S. A., Image segmentation using Markov random field models, Dissertation, University of Cambridge, 1998.

Christopher, L., Bayesian segmentation of three dimensional images using the EM/MPM algorithm, Dissertation, Purdue University, 2003.

De Prisco et al., Digital rock analysis systems and methods that reliably predict a porosity-permeability trend, Provisional U.S. application Ser. No. 61/692,541.

Durlofsky, L. J., Upscaling and gridding of fine scale geological models for flow simulation, 8th International Forum on Reservoir Simulation, 2005.

Ehrenberg, S. N., Nadeau, P. H., Sandstone vs. carbonate petroleum reservoirs: A global perspective on porosity-depth and porosity-permeability relationships, AAPG Bulletin, v. 89, no. 4, 2005.

Ehrenberg, S. N., Whole core versus plugs: Scale dependence of porosity and permeability measurements in platform carbonates, AAPG Bulletin, 91(6), 2007.

Green, C. P., and Paterson, L., Analytical three-dimensional renormalization for calculating effective permeabilities, Transport in Porous Media, 68(2), 2007.

Khalili, A. D., Arns, J.-Y., Hussain, F., Cinar, Y., Pinczewski, W. V., Latham, D., Funk, J., Permeability upscaling for carbonates from the pore-scale using multi-scale Xray-CT images, SPE 152640, 2012.

Khalili, A. D., Yanici, S., Cinar, Y., Arns, C. H., Formation factor for heterogeneous carbonate rocks using multi-scale Xray-CT images, Journal of Engg. Research, Year 1, No. 2, 2013.

Krabbenhoft, K., Karim, M. R., New renormalization schemes for conductivity upscaling in heterogeneous media, Transport in Porous Media, 85(3), 2010.

Liang, M., 3D co-occurrence matrix based texture analysis applied to cervical cancer screening, Dissertation, Uppsala Universitet, 2012.

Ma, S., Morrow, N. R., Relationships between porosity and permeability for porous rocks, 1996 SCA Conference paper number 9610.

Nelson, P. H., Permeability-porosity relationships in sedimentary rocks, 1994, The Log Analyst (May-June), 38-62.

Ramstad, T., Oren, P.-E., Bakke, S., Simulation of two-phase flow in reservoir rocks using a lattice Boltzmann method, SPE Journal, SPE 124617, 2010.

Sungkorn et al., Method for Establishing Petrophysical Trends Using Digital Rock Physics Imaging, 2014a.

Sungkorn et al., A Method for Determination of Representative Elementary Volume using Advanced Statistical Analysis, 2014b.

Torabi, A., Fossen, H., Braathen, A., Insight into petrophysical properties of deformed sandstone reservoirs, AAPG Bulletin, v. 97, no. 4, 2013.

Unser, M., Eden, M., Multiresolution feature extraction and selection for texture segmentation, IEEE transactions on pattern analysis and machine intelligence, 11(7), 1989.

Vik, B., Bastesen, E., Skauge, A., Evaluation of representative elementary volume for vuggy carbonate rock— Part: Porosity, permeability, and dispersivity, Journal of Petroleum Science and Engineering, 112, 2013.

Weibel, R., Kristensen, L., Olivarius, M., Hjuler, M. L., Mathiesen, A., Nielsen, L. H., Investigating deviations from overall porosity-permeability trends, Proceedings Thirty-Sixth Workshop on Geothermal Reservoir Engineering, 2012.

Worthington, P. F., The effect of scale on the petrophysical estimation of intergranular permeability, Petrophysics 45(1), 2004.

What is claimed is:

1. A method that comprises:
acquiring a two-dimensional (2D) or three-dimensional (3D) digital image of a rock sample;
selecting a subsample within the digital image;
deriving a trend for the subsample, wherein the trend comprises a relationship between petrophysical properties of the subsample;
applying the trend to a larger-scale portion of the digital image; and
performing subsequent analysis of the digital image based on the applied trend.

2. The method of claim 1, wherein selecting the subsample comprises identifying a fully-resolved entity within the digital images and selecting the fully-resolved entity as the subsample.

3. The method of claim 2, further comprising performing a statistical analysis to identify the fully-resolved entity.

4. The method of claim 2, further comprising performing image-processing to identify the fully-resolved entity.

5. The method of claim 1, wherein selecting the subsample comprises identifying an unresolved entity within the digital images, obtaining a higher-resolution image of the unresolved entity, identifying a fully-resolved entity within the higher-resolution image, and selecting the fully-resolved entity as the subsample.

6. The method of claim 1, further comprising relating a property value of the larger-scale sample to the trend or petrophysical property.

7. The method of claim 1, further comprising deriving a trend or petrophysical property for each of a plurality of subsamples, and applying an aggregation of the trends or petrophysical properties to a larger-scale portion of the digital images.

8. The method of claim 1, wherein deriving a trend or petrophysical property comprises deriving a multi-modal distribution of property measurements.

9. The method of claim 1, wherein deriving a trend for the subsample comprises determining a distribution of property measurements and extracting component distributions.

10. The method of claim 1, further comprising:
acquiring additional 2D or 3D digital images of the rock sample;
selecting an additional subsample within the digital images;
deriving an additional trend for the subsample;
applying the additional trend to the larger-scale portion of the digital images; and
performing subsequent analysis of the digital images based on the applied additional trend.

11. A system that comprises:
a memory having software; and
one or more processors coupled to the memory to execute the software, the software causing the one or more processors to:
acquire a two-dimensional (2D) or three-dimensional (3D) digital image of a rock sample;
select a subsample within the digital image;
derive a trend for the subsample, wherein the trend comprises a relationship between petrophysical properties of the subsample; and
apply the trend to a larger-scale portion of the digital image;
performing subsequent analysis of the digital images based on the applied trend.

12. The system of claim 11, wherein the software causes the one or more processors to select the subsample by identifying a fully-resolved entity within the digital images and by selecting the fully-resolved entity as the subsample.

13. The system of claim 12, wherein the software causes the one or more processors to perform a statistical analysis to identify the fully-resolved entity.

14. The system of claim 12, wherein the software causes the one or more processors to perform image-processing to identify the fully-resolved entity.

15. The system of claim 11, wherein the software causes the one or more processors to select the subsample by identifying an unresolved entity within the digital images, obtaining a higher-resolution image of the unresolved entity, identifying a fully-resolved entity within the higher-resolution image, and selecting the fully-resolved entity as the subsample.

16. The system of claim 11, wherein the software further causes the one or more processors to relate a property value of the larger-scale sample to the trend or petrophysical property.

17. The system of claim 11, wherein the software causes the one or more processors to derive a trend or petrophysical property for each of a plurality of subsamples, and to apply an aggregation of the trends or petrophysical properties to a larger-scale portion of the digital images.

18. The system of claim 11, wherein the software further causes the one or more processors to deriving a trend or petrophysical property by deriving a multi-modal distribution of property measurements.

19. The system of claim 11, wherein the software further causes the one or more processors to derive a trend for the subsample by determining a distribution of property measurements and extracting component distributions.

20. The system of claim 11, wherein the software further causes the one or more processors to perform subsequent analysis of additional digital images based on the applied trend.

* * * * *